(12) United States Patent
Soga et al.

(10) Patent No.: US 6,371,949 B1
(45) Date of Patent: Apr. 16, 2002

(54) DISPOSABLE BODY FLUIDS ABSORBENT GARMENT WITH DISPOSAL SECURING MEANS

(75) Inventors: Hiroyuki Soga; Toshio Inoue, both of Kagawa-ken; Hirotomo Mukai, Kawanoe; Yoshikazu Takigawa, Kagawa-ken, all of (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 09/014,615

(22) Filed: Jan. 28, 1998

(30) Foreign Application Priority Data

Jan. 31, 1997 (JP) ................................. 9-018040

(51) Int. Cl.$^7$ ........................... A61F 13/15; A61F 13/20
(52) U.S. Cl. ................... 604/385.13; 604/390
(58) Field of Search ..................... 604/385.1, 386, 604/387–391, 393–396, 385.01, 385.13

(56) References Cited

U.S. PATENT DOCUMENTS

| | | | |
|---|---|---|---|
| 2,931,747 A | * | 4/1960 | Dexter |
| 4,207,895 A | * | 6/1980 | Schaar |
| 4,670,012 A | * | 6/1987 | Johnson |
| 4,778,701 A | * | 10/1988 | Pape et al. |
| 5,575,784 A | * | 11/1996 | Ames-Ooten et al. |
| 5,582,294 A | | 12/1996 | Yamada |

FOREIGN PATENT DOCUMENTS

| | | |
|---|---|---|
| EP | 0 314 535 | 5/1989 |
| EP | 0 338 680 | 10/1989 |
| EP | 0 732 094 | 9/1996 |
| GB | 1186787 | 4/1970 |
| GB | 1449265 | 9/1976 |
| JP | 58-22908 | 2/1983 |
| WO | 94/09736 | 5/1994 |

* cited by examiner

Primary Examiner—K. M. Reichle
(74) Attorney, Agent, or Firm—Lowe Hauptman Gilman & Berner, LLP

(57) ABSTRACT

Disposal securing arrangements provided on a backsheet of body fluids absorbent garment for disposal thereof has a first strip section bonded to the backsheet, a second strip section bonded to the backsheet, a third strip section having a proximal end portion connected to at least one of the first and second strip sections, and a free end portion. The third strip section includes a stretchable extent defined between these opposite end portions. The third strip section is separably held against the first strip section by a securing region provided thereon. The first and second section strip sections respectively have holding forces sufficient to remain held against the backsheet as the third strip section is peeled off from the first strip section and stretched. The holding force generated in the first strip section is equal to or higher than the holding force generated in the second strip section.

2 Claims, 2 Drawing Sheets

DISPOSABLE BODY FLUIDS ABSORBENT GARMENT WITH DISPOSAL SECURING MEANS

The present application is a continuation-in-part of application Ser. No. 08/917,928, filed Aug. 27, 1997, entitled "DISPOSABLE BODY FLUIDS ABSORBENT ARTICLE HAVING DISPOSAL SECURING MEANS".

BACKGROUND OF THE INVENTION

This invention relates generally to a disposable body fluid absorbent garment and more particularly to such a garment provided with means for securing the garment in a rolled up state convenient for disposal thereof.

Japanese Laid-Open Utility Model Application No. Sho58-22908 discloses a disposable diaper provided with disposal securing means for securing the diaper in a rolled up or folded state after it has been removed from a wearer. Such disposal securing means is effective to prevent any stained portion of the diaper from being exposed. Therefore, the used diaper can be disposed in a manner which is preferable from both aesthetic and sanitary viewpoints.

A diaper disclosed in EP 0 732 094 A2 uses longitudinally stretchable or elastic disposal securing means for disposal of the diaper. Such disposal securing means can be conveniently maintained to be relatively short before its actual use so that the diaper may be put on or removed from a wearer without being obstructed by the presence of the disposal securing means.

Generally, such disposal securing means made of a stretchable or elastic strip of tape is stretched and secured around the used diaper, which has been conveniently rolled up for disposal, by fixing an end of the disposal securing means to a surface of the used diaper. As the disposal securing means is stretched, tension in the disposal securing means tends to peel the disposal securing means end off the surface. Accordingly, excessively weak fixation of the end of the disposal securing means may cause this end to be readily peeled off the used diaper, and excessively firm fixation may cause a sheet forming the surface of the diaper to be torn as the means is stretched, resulting in exposure of an absorbent core of the diaper smeared with excretion and/or leakage of excretion's malodor from the absorbent core.

SUMMARY OF THE INVENTION

Therefore, it is a principal object of the invention to improve the disposal securing means for securing a garment, such as a diaper, in a rolled up or folded state for disposal so that the disposal securing means can neither be completely peeled off the garment nor tear the garment surface.

The object set forth above is achieved, according to an aspect of the invention, by a disposable body fluid absorbent garment having a skin-contactable surface intended to be in contact with the skin of a wearer, and a skin-non-contactable surface provided with disposal securing means being stretchable at least in one direction in order to be secured around the garment which has been rolled up for disposal.

The disposal securing means comprises a substantially non-stretchable first strip section having inner and outer surfaces and first and second end portions, a substantially non-stretchable second strip section having inner and outer surfaces and first and second end portions, and a third strip section having inner and outer surfaces and proximal and free end portions. The free end portion is provided on the inner surface of the third strip section with a securing region. The third strip section further includes a stretchable extent defined between the proximal and free end portions. The first and second strip sections have the respective inner surfaces which are bonded to the skin-non-contactable surface so that these two strip sections are longitudinally aligned with each other. The first end portion of the first strip section is connected between the first and second end portions of the second strip section. The third strip section has the proximal end portion connected to at least one of the respective first end portions of the first and second strip sections, and the securing region provided on the free end portion of the third strip section is separably held against the outer surface of the first strip section in the proximity of its second end portion.

The first, second and third strip sections have holding forces $H_1$, $H_2$ and $H_3$, respectively, for holding them against the skin-non-contactable surface. The holding force $H_1$ is sufficient to hold the first strip section against the skin-non-contactable surface against a stretching stress generated in the third strip section as the third strip section is peeled off the first strip section, stretched and held against the skin-non-contactable surface with the securing region. The respective holding forces are selected so that $H_3 > H_1 \geq H_2$, wherein the holding force $H_2$ is selected so that the second strip section may be peeled off the skin-non-contactable surface before the skin-non-contactable surface is torn.

According to another aspect of the invention, the object set forth above is achieved by a disposable body fluid absorbent garment having a skin-contactable surface intended to be in contact with the skin of a wearer, and a skin-non-contactable surface provided with disposal securing means being stretchable at least in one direction in order to be secured around the garment which has been rolled up for disposal.

The disposal securing means comprises a substantially non-stretchable strip section having inner and outer surfaces and first and second end portions, and a stretchable strip section having inner and outer surfaces and proximal and free end portions. The free end portion is provided on the inner surface of the stretchable strip section with a securing region. The stretchable strip section further has a stretchable extent defined between the proximal and free end portions. The first and second end portions of the non-stretchable strip section are directly attached to the skin-non-contactable surface with discrete first and second adhesive portions, respectively, for holding the non-stretchable strip section against the skin-non-contactable surface by respective holding forces $h_1$, and $h_5$. The stretchable strip section has its proximal end portion connected to the first end portion of the non-stretchable strip section strip section, and the securing region is separably held against the non-stretchable strip section in the proximity of its second end portion.

The holding force $h_5$ generated in the second adhesive portion is sufficient to hold the non-stretchable strip section against the skin-non-contactable surface against a stretching stress generated in the stretchable strip section as the stretchable strip section is peeled off the non-stretchable strip section, stretched and held against the skin-non-contactable surface, to maintain the garment in a rolled configuration with a holding force $H_3$ of the securing region, after use. The holding forces are selected so that $H_3 > h_5 \geq h_1$. The holding force $h_1$ is selected to enable release of the first adhesive portion from the skin-non-contactable surface before the skin-non-contactable surface is torn.

DESCRIPTION OF THE PREFERRED EMBODIMENT

Details of a disposable body fluid absorbent garment according to the present invention will be more fully understood from the following description of a disposable diaper exemplarily given hereunder in reference with the accompanying drawings.

Figure 1:
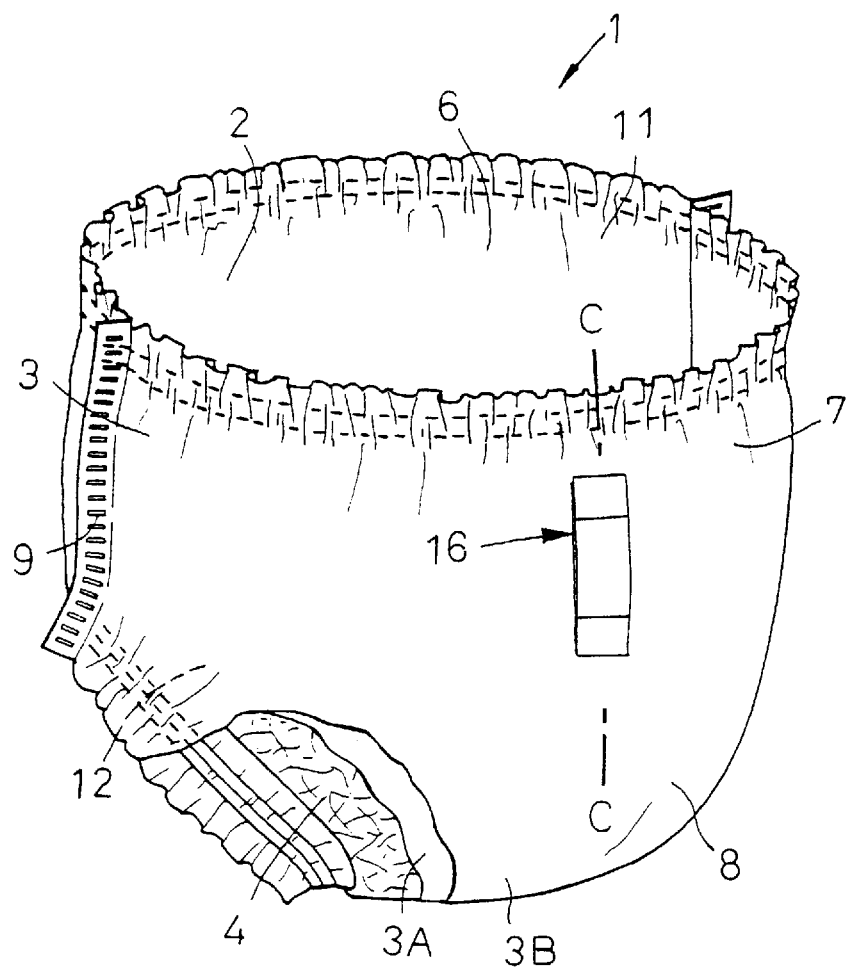
FIG. 1 is a partially broken away, perspective view showing a disposable diaper, as a disposable body fluid absorbent garment, according to an embodiment of the invention.

A disposable diaper 1 shown by FIG. 1 in a perspective view as partially broken away is of a pull-on or shorts-type. The disposable diaper 1 comprises a liquid-permeable topsheet 2 formed by a nonwoven fabric made of thermoplastic synthetic fibers, a first liquid-impermeable backsheet 3A formed by a thermoplastic synthetic resin film, a second backsheet 3B formed by a nonwoven fabric and intermittently bonded to an outer surface of the first backsheet 3A by means of hot melt adhesive (not shown), and a liquid-absorbent core 4 disposed between the topsheet 2 and the first backsheet 3A. The diaper 1 is composed of a front waist region 6, a rear waist region 7, and a crotch region 8 extending between these two regions 6, 7. The topsheet 2, the first and second backsheets 3A, 3B are substantially identical to one another in shape and in size, and the first and second backsheets 3A, 3B together define a backsheet 3. The topsheet 2 and the backsheet 3 are bonded to each other by means of hot melt adhesive (not shown) at the portions outside the peripheral edge of the absorbent core 4. The transversely opposite side edges of the front and rear waist regions 6, 7 are welded to each other at a plurality of spots 9 intermittently arranged in the longitudinal direction so as to define a waist-opening 11 and a pair of leg-openings 12. The rear waist region 7 is provided, on a center line C—C dividing the region 7 in right and left halves, with disposal securing means 16 for securing the diaper 1 in a rolled up or folded state after it has been removed from a wearer.

Figure 2:
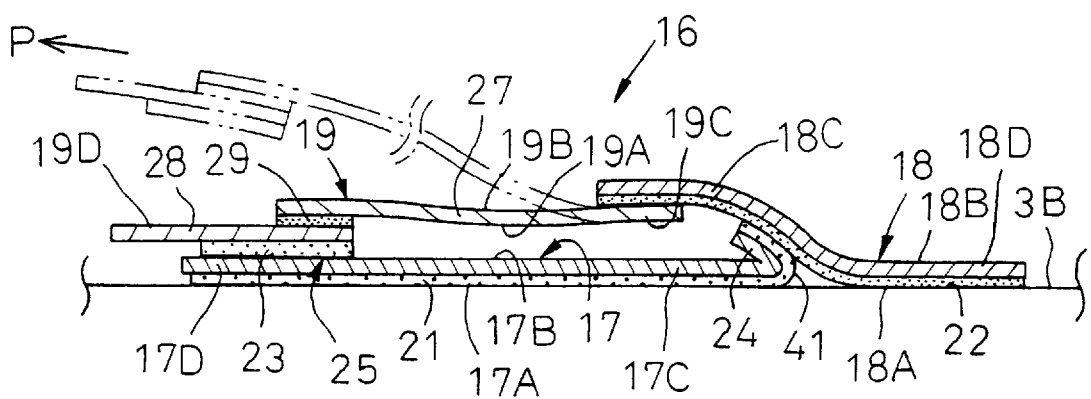
FIG. 2 is a fragmentary sectional view taken along the line C—C in FIG. 1.

FIG. 2 is a sectional view taken along the line C—C in FIG. 1, showing the disposal securing means 16. The disposal securing means 16 comprises a first strip section 17 having inner and outer surfaces 17A, 17B and first and second end portions 17C, 17D, respectively; a second strip section 18 having inner and outer surfaces 18A, 18B and first and second end portions 18C, 18D, respectively; and a third strip section 19 having inner and outer surfaces 19A, 19B and proximal and free end portions 19C, 19D, respectively. The first, second and third strip sections 17, 18, 19 are identical to one another in width.

The first strip section 17, made of a substantially non-stretchable material, extends longitudinally (as viewed in FIG. 1) of the diaper 1. The inner surface 17A is bonded to an outer surface of the second backsheet 3B by means of a first glue layer 21. A part of the first end portion 17C, located at a lower portion of the diaper 1, is folded upward. In this manner, the first strip section 17 is caused to define a turn-up line 41. The first strip section 17 and the second strip section 18 are longitudinally aligned with each other so that the respective first end portions 17C, 18C overlie each other. The first end portion 17C is connected to the second strip section 18 at an intermediate location between the first and second end portions 18C, 18D of the second strip section 18.

The second strip section 18 is made of a non-stretchable material and its inner surface 18A is bonded to the outer surface of the second backsheet 3B by means of a second glue layer 22. The folded part 24 of the first strip section 17 is bonded to the inner surface 18A of the second strip section 18 by means of the first and second glue layers 21, 22. The unique manner in which the folded part 24 is bonded to the second strip section 18 allows the turn-up line 41 to be effectively covered with the second strip section 18. The turn-up line 41 covered in this manner does not define a sharp corner which otherwise will tend to irritate the skin of a wearer.

The third strip section 19 comprises a stretchable portion 27 made of a stretchable material, and a non-stretchable portion 28 made of a non-stretchable material. These two portions 27, 28 are bonded to each other by means of a fourth glue layer (or adhesive layer) 29. The proximal end portion 19C of the third strip section 19 corresponds to a lower end portion (a right end portion as viewed in FIG. 2) and may be connected to the first end portion 17C or 18C of one of the first and second strip sections 17, 18. In FIG. 2 the proximal end portion 19C is illustrated as being connected to the first end portion 18C by means of the second glue layer 22. The free end portion 19D of the third strip section 19 includes the non-stretchable portion 28 and extends upwardly of the diaper 1 beyond the second end portion 17D of the first strip section 17 so as to be easily picked up by a user. The inner surface 19A of the free end portion 19D is partially coated with a third glue layer 23 to define a securing region 25 which is, in turn, releasably bonded onto the outer surface 17B of the first strip section 17.

Figure 3:
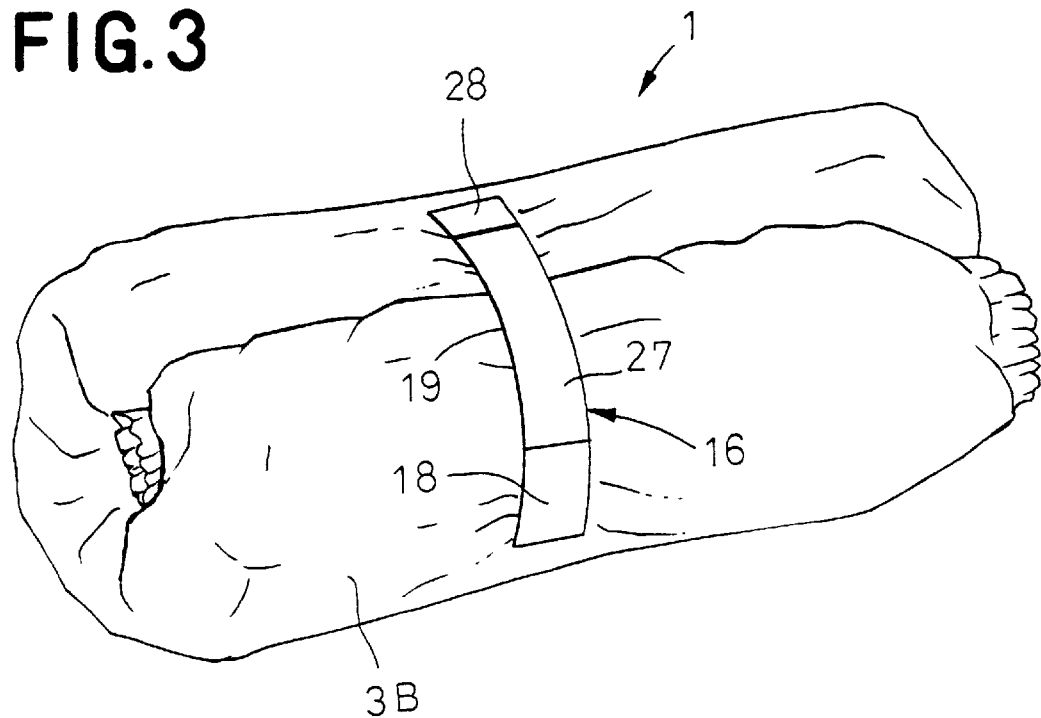
FIG. 3 is a perspective view showing the diaper in a rolled up state.

FIG. 3 is a perspective view showing the diaper 1 secured in the rolled up state using the disposal securing means 16. The free end portion 19D is held by fingers of a user, peeled off the outer surface 17B of the first strip section 17, and pulled in a direction indicated by an arrow P in FIG. 2 (i.e., upwardly of the diaper 1 as viewed in FIG. 1) to stretch the stretchable portion 27. The disposal securing means 16 thus stretched is secured around the rolled up diaper 1 and the securing region 25 is held against the diaper 1 at an appropriate location, for example, on the second backsheet 3B. In this way, the disposal securing means 16 secures the diaper 1 smeared with excretion in a ready for disposal state, without exposing the portions of the diaper smeared with excretion.

In the disposal securing means 16, the stretchable portion 27 of the third strip section 19 is firmly bonded to the non-stretchable portion 28, on one hand, and to the second strip section 18, on the other hand, in a substantially inseparable manner. The second strip section 18 and the first strip section 17 are also bonded to each other in a substantially inseparable manner.

After the third strip section 19 has been peeled off the first strip section 17, then stretched in the direction P and held at the securing region 25 against the second backsheet 3B of the rolled up diaper 1, the first, second and third strip sections 17, 18, 19 hold their initial places on the second backsheet 3B. Assuming that the sections 17, 18, 19 have holding forces $H_1$, $H_2$, $H_3$, respectively, these holding forces should be in a relationship of $H_3 > H_1 \geq H_2$. In addition, when the disposal securing means 16 are pulled in the direction P, the holding force $H_2$ of the second strip section 18 is preferably selected so that the second section 18 may be peeled off the second backsheet 3B before the second backsheet 3B is torn. The holding force $H_1$ of the first strip section 17 should be equal to or higher than the holding force $H_2$. Once the second strip section 18 has been peeled off, the disposal securing means 16 are held by the first strip section 17 on the second backsheet 3B. Further pulling the disposal securing means 16 from this state in the direction P may cause the first strip section 17 to be partially peeled off the second backsheet 3B. However, the more the first strip section 17 is peeled from the second backsheet 3B, the less the tension of the disposal securing means 16 becomes, and finally the means 16 ceases to be further peeled off the second backsheet 3B. The holding forces $H_1$, $H_2$, $H_3$ are generated as a result of bonding the respective strip sections 17, 18, 19 to the second backsheet 3B by means of first, second and third glue layers 21, 22, 23, respectively. Levels of the respective holding forces $H_1$, $H_2$, $H_3$ can be adjusted by selecting their adhesive powers and/or selecting areas coated with the glue layers 21, 22, 23. It should be understood that the holding force $H_3$ of the third strip section 19 depends on a force with which the securing region 25 is held against the second backsheet 3B. The securing region 25 is preferably constructed so that the requirement of $H_3>H_1 \geq H_2$ is satisfied even when the securing region 25 is held against the second backsheet 3B with a slight pressure.

Figure 4:
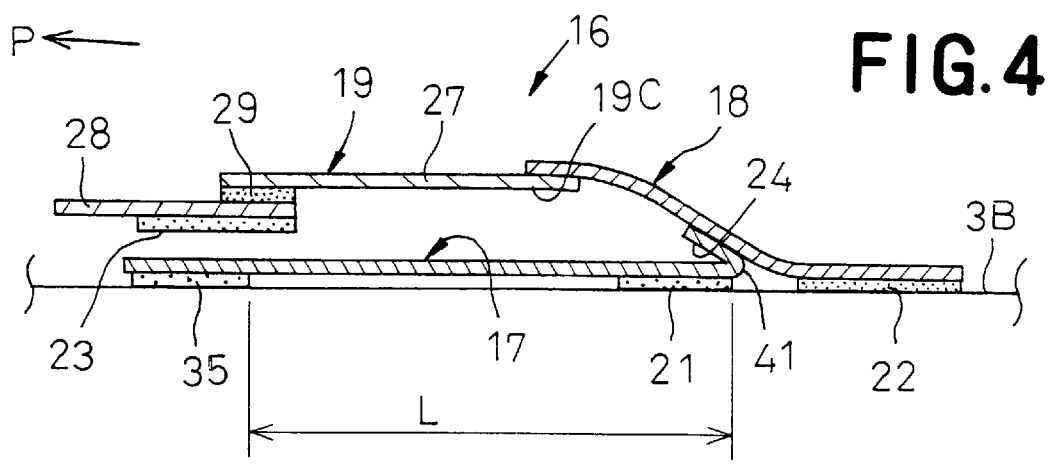
FIG. 4 is a view similar to FIG. 2, showing another embodiment the invention.

FIG. 4 is a view similar to FIG. 2 showing another embodiment of the disposal securing means 16 according to the invention. According to this embodiment, the first strip section 17 is bonded to the second backsheet 3B by means of the first glue layer 21 and a fifth glue layer 35. The lower part 24 (i.e., the rightmost part as viewed in FIG. 4) of the first strip section 17 is bonded to the second strip section 18 by means of heat-sealing, and the proximal end portion 19C of the third strip section 19 is also bonded to the second strip section 18 by means of heat-sealing. Accordingly, the strip sections 17, 18, 19 are bonded to one another in a substantially inseparable fashion. The holding force $H_1$ of the first strip section 17 for the second backsheet 3B can be considered to be a sum of a holding force $h_1$ provided by the first glue layer 21 and a holding force $h_5$ provided by the fifth glue layer 35. The holding force $h_1$ of the first glue layer 21 is such that the first glue layer 21 can be released from the second backsheet 3B as the disposal securing means 16 continues to be pulled in the direction P after the second strip section 18 has been peeled off the second backsheet 3B. The holding force $h_5$ of the fifth glue layer 35 is equal to or higher than the holding force hi of the first glue layer 21. More particularly, the holding forces are selected so that $H_3>h_5 \geq h_1$, where $H_3$ is the holding force of the third strip section 19. In the course of fastening the disposal securing means 16 with a high tension around the used diaper 1, the second glue layer 22 and the first glue layer 21 are successively released from the second backsheet 3B in this order. Thereupon a length of the disposal securing means 16 secured around the used diaper 1 is prolonged by a length L defined by the distance between the first glue layer 21 and the fifth glue layer 35 of the first strip section 17. Consequently, the disposal securing means 16 contracts by the length L. This contraction and the high holding force $h_5$ of the fifth glue layer 35 contribute to hold the disposal securing means 16 around the used diaper 1.

Figure 5:
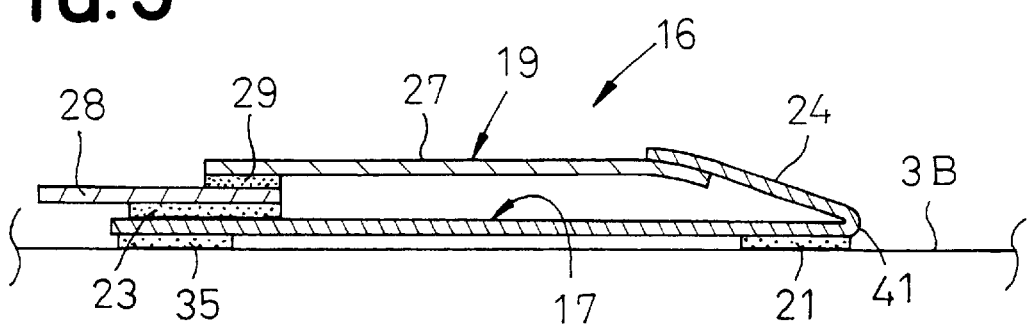
FIG. 5 is a view similar to FIG. 2, showing still another embodiment of the invention.

FIG. 5 is a view similar to FIG. 2 showing still another embodiment of the disposal securing means 16. According to this embodiment, the disposal securing means 16 comprises only the first non-stretchable strip section 17 and a stretchable strip section 19 corresponding to the third strip section 19 in the embodiment shown by FIG. 4. While the first strip section 17 is of the same arrangement as that shown by FIG. 4, the stretchable strip section 19 is different from the strip section 19 shown by FIG. 4 in that the stretchable portion 27 is bonded to the folded-back portion 24. The first strip section 17 is bonded to the second backsheet 3B by means of the first glue layer 21 and the fifth glue layer 35 which are spaced apart from each other. The holding force $h_5$ of the fifth glue layer 35 is equal to or higher than the holding force $h_1$ of the first glue layer 21. The first glue layer 21 is released from the second backsheet 3B as the stretchable strip section 19 is stretched with an excessive tension, and thereupon the stretchable strip section 19 is caused to contract. On the other hand, the first strip section 17 remains held by the holding force $h_5$ of the fifth glue layer 35 on the used diaper 1 just as in the case of the embodiment shown by FIG. 4. Note again that the holding forces are selected so that $H_3>h_5 \geq h_1$, where $H_3$ is the holding force of the third strip section 19. With the disposal securing means 16 according to this embodiment, the first strip section 17 is preferably made of a soft material in order to avoid a possibility that the turn-up line 41 of this first strip section 17 might define sharp corner tending to irritate the skin of a wearer, since the turn-up line 41 defined by the folded-back portion 24 of the first strip section 17 may directly touch the skin of the wearer.

The disposal securing means 16 according to the invention can be used not only for the disposable diaper 1 of pull-up or shorts type but also for other disposable body fluid absorbent garments, such as open type diapers, training pants, incontinence pants, urine absorbent pads and bandages. The stretchable portion 27 of the stretchable strip section 19 may be elastically stretchable or inelastically stretchable. In order to assure that the first glue layer 21 as well as the second glue layer 22 can be released from the second backsheet 3B, in addition to adjustment of the adhesive powers provided by these first and second glue layers 21, 22, the second backsheet 3B may be appropriately surface-treated and thereby releasability of the first and second glue layers 21, 22 may be adjusted. While the backsheet 3 of the diaper 1 is illustrated as a laminate of the plastic film 3A and the nonwoven fabric 3B, it is also possible to form the backsheet 3 by any one of the plastic film 3A and the nonwoven fabric 3B. While the disposal securing means 16 is illustrated to be stretched upwardly of the diaper 1, the direction in which the disposal securing means 16 are stretched is selective, for example, downwardly or transversely of the diaper 1.

The third glue layer 23 provided on the third strip section 19 may be replaced by the mechanical fastener commonly known under the trademark of MAGIC TAPE or VELCRO. It should be understood that, if the mechanical fastener is adopted, the first strip section 17 and the second backsheet 3B should be made of a specific material against which the mechanical fastener can be reliably held.

With the disposable body fluid absorbent garment according to the invention, the stretchable disposal securing means, used to secure the garment in a rolled up state for disposal, is attached to the backsheet of the garment in a partially separable fashion. As a result, the disposal securing means is partially separated from the backsheet and relaxed as the disposal securing means is pulled with an excessive tension. In this manner, a rupture or other various damages possibly occurring in the backsheet can be reliably avoided.

What is claimed is:

1. A disposable body fluids absorbent garment comprising a skin-contactable surface adapted to contact a wearer's skin, a core disposed adjacent the skin-contactable surface and through which surface body fluids discharged by the wearer are absorbed by the core, and a skin-non-contactable surface disposed opposite the skin-contactable surface with the core sandwiched therebetween, said skin-noncontactable surface supporting a disposal securing arrangement being stretchable at least in one direction in order to be secured around the garment which has been rolled up for disposal, said skin-contactable and non-skin-contactable surfaces each having transversely extending edges at longitudinal opposite ends thereof that define the longitudinal extent of the garment, wherein said disposal securing arrangement includes a substantially non-stretchable first strip section having an inner surface and an outer surface and a first end portion and a second end portion, a substantially non-stretchable second strip section having an inner surface and an outer surface and a first end portion and a second end portion, and a third strip section having an inner surface and an outer surface and a proximal end portion and a free end portion, wherein the free end portion includes a securing region provided on the inner surface of the third strip section, said securing region containing an adhesive to releasably hold the securing region against the outer surface of the first strip section in the proximity of its second end portion; and said third strip section further including a stretchable extent defined between the proximal and free end portions;

the first and second strip sections have the respective inner surfaces directly attached by bonding to the skin-non-contactable surface so that these two strip sections extend perpendicular to said transversely extending edges and are longitudinally aligned with each other and have their respective first end portions longitudinally opposed to each other, the first end portion of the first strip section being directly attached to the inner surface of the second strip section between the first and second end portions of the second strip section, said proximal end portion being directly attached to one of the respective first end portions of the first and second strip sections; and the first, second and third strip sections have holding forces, H1, H2, H3, respectively, for holding them against the skin-non-contactable surface, the holding forces H1 and H3 being sufficient to hold the corresponding strip section against the skin-non-contactable surface against a stretching stress generated in the third strip section as the securing region of the third strip section is peeled off the outer surface of the first strip section, stretched and adhesively attached to the skin-non-contactable surface of the garment to maintain the garment in a rolled configuration with the holding force H3, after use, the holding forces being selected so that the holding force H1 achieved by said bonding of the first strip section to the skin-non-contactable surface is equal to or greater than the holding force H2 achieved by said bonding of the second strip section to said skin-non-contactable surface, the holding force H3 is selected so that H3>H1≧H2, wherein the holding force H2 is selected so that the second strip section may be peeled off the skin-non-contactable surface without tearing said skin-non-contactable surface.

2. A disposable body fluids absorbent garment comprising a skin-contactable surface adapted to contact a wearer's skin, a core disposed adjacent the skin-contactable surface and through which surface body fluids discharged by the wearer are absorbed by the core, and a skin-non-contactable surface disposed opposite the skin-contactable surface with the core sandwiched therebetween; said skin-non-contactable surface supporting a disposal securing arrangement being stretchable at least in one direction in order to be secured around the garment which has been rolled up for disposal, said skin-contactable and skin-non-contactable surfaces each having transversely extending edges at longitudinal opposite ends thereof that define the longitudinal extent of the garment, wherein said disposal securing arrangement includes a substantially non-stretchable strip section having inner and outer surfaces and first and second end portions, said first and second end portions being directly attached to the skin-non-contactable surface with discrete first and second adhesive portions, respectively, for holding the non-stretchable strip section against the skin-non-contactable surface by respective holding forces H1 and H5, and a stretchable strip section having inner and outer surfaces and proximal and free end portions, that jointly extend perpendicular to said transversely extending edges wherein the free end portion is provided on the inner surface of the stretchable strip section with a securing region, said stretchable strip section having a stretchable extent defined between the proximal and free end portions thereof;

said proximal end portion being directly attached to the first end portion of the non-stretchable strip section and the securing region provided on the free end portion being releasably held against the non-stretchable strip section in the proximity of its second end portion; and the holding force H5 being sufficient to hold the non-stretchable strip section against the skin-non-contactable surface against a stretching stress generated in the stretchable strip section as the stretchable strip section is peeled off the non-stretchable strip section, stretched and held against the skin-non-contactable surface, to maintain the garment in a rolled configuration after use, the holding force H5 generated in the second adhesive portion is equal to or higher than the holding force H1 generated in the first adhesive portion, i.e. H5≧H1, wherein the holding force H1 is selected to enable release of the first adhesive portion from the skin-non-contactable surface without tearing said skin-non-contactable surface.

* * * * *